US005756833A

United States Patent [19]

Rosen et al.

[11] Patent Number: 5,756,833
[45] Date of Patent: *May 26, 1998

[54] CATALYTIC PURIFICATION AND RECOVERY OF DICARBOXYLIC AROMATIC ACIDS

[75] Inventors: Bruce I. Rosen, Morton Grove; Thomas M. Bartos, Naperville, both of Ill.

[73] Assignee: Amoco Corporation, Chicago, Ill.

[*] Notice: The term of this patent shall not extend beyond the expiration date of Pat. No. 5,616,792.

[21] Appl. No.: 778,297

[22] Filed: Jan. 2, 1997

Related U.S. Application Data

[63] Continuation-in-part of Ser. No. 595,046, Feb. 1, 1996, Pat. No. 5,616,792.

[51] Int. Cl.$^6$ .................................................. C07C 51/42
[52] U.S. Cl. ............................ 562/486; 562/485; 562/412
[58] Field of Search ............................. 562/486, 412, 562/485

[56] References Cited

U.S. PATENT DOCUMENTS

| | | |
|---|---|---|
| 3,584,039 | 6/1971 | Meyer. |
| 3,726,915 | 4/1973 | Pohlmann. |
| 4,201,872 | 5/1980 | Kimura et al.. |
| 4,317,923 | 3/1982 | Imai. |
| 4,394,299 | 7/1983 | Puskas et al.. |
| 4,405,809 | 9/1983 | Stech et al.. |
| 4,467,110 | 8/1984 | Puskas et al.. |
| 4,629,715 | 12/1986 | Schroeder. |
| 4,652,674 | 3/1987 | James et al.. |
| 4,743,577 | 5/1988 | Schroeder et al.. |
| 4,831,008 | 5/1989 | Timmer et al.. |
| 4,892,972 | 1/1990 | Schroeder et al.. |
| 5,292,934 | 3/1994 | Sikkenga et al.. |
| 5,362,908 | 11/1994 | Schroeder et al.. |
| 5,616,792 | 4/1997 | Bartos et al. ........................ 562/486 |

FOREIGN PATENT DOCUMENTS 8274278  7/1978  Japan.

Primary Examiner—Samuel Barts
Attorney, Agent, or Firm—Thomas E. Nemo; Wallace L. Oliver; Frederick S. Jerome

[57] ABSTRACT

Processes using a titanium dioxide-supported purification catalyst are disclosed for purification of relatively impure dicarboxylic aromatic acid produced by liquid-phase oxidation of a suitable benzene or naphthalene having two oxidizable ring substituents, and/or by recovery from polyester resin comprising repeating units of the dicarboxylic aromatic acid residue and repeating units of dihydric alcohol residue. Purification comprises passing an aqueous solution of dicarboxylic aromatic acid with small amounts of organic impurities consisting of oxygen-containing aromatic co-products of oxidation and/or other organic components, through a particulate bed of purification catalyst comprising a noble metal on a titanium dioxide support under conditions suitable for decarbonylation of organic impurities. Generally, at least one weight percent of the titanium dioxide support is in the rutile crystalline phase. Optionally, effluent aqueous solution from the bed containing noble metal on the titanium dioxide support is passed through a subsequent particulate bed of another purification catalyst in the presence of a molecular hydrogen-containing gas. Hydrogenation of the aqueous solution subsequent to decarbonylation further reduces organic impurities in dicarboxylic aromatic acid recovered by crystallization and separation from the aqueous solution.

The invention provides improved processes for preparation of purified terephthalic acid wherein purified terephthalic acid product is recovered from its mother liquor while maintaining temperatures within a range downward from about 100° C. to about 25° C. and pressures near or at atmospheric pressure.

9 Claims, No Drawings

5,756,833

CATALYTIC PURIFICATION AND RECOVERY OF DICARBOXYLIC AROMATIC ACIDS

CROSS-REFERENCE TO RELATED APPLICATIONS

This application is a continuation-in-part of application Ser. No. 08/595,046 filed Feb. 1, 1996, now U.S. Pat. No. 5,616,792 which is specifically incorporated herein, in its entirety, by reference.

FIELD OF THE INVENTION

The field of this invention relates to use of titanium dioxide-supported purification catalysts in purification of relatively impure dicarboxylic aromatic acid produced by liquid-phase oxidation of a suitable benzene or naphthalene having two oxidizable ring substituents, and recovery from polyester resin comprising repeating units of the dicarboxylic aromatic acid residue and repeating units of dihydric alcohol residue. More particularly, this invention concerns purification by passing an aqueous solution of dicarboxylic aromatic acid with small amounts of organic impurities consisting of oxygen-containing aromatic co-products of oxidation and/or other organic components, through a particulate bed of purification catalyst comprising at least one noble metal supported on a carrier comprising titanium dioxide under conditions suitable for decarbonylation of organic impurities. At least a portion of the titanium dioxide support is, advantageously, in the rutile crystalline phase.

Optionally, effluent aqueous solution from the bed containing noble metal on a titanium dioxide support is passed through a subsequent particulate bed of another purification catalyst in the presence of a molecular hydrogen-containing gas. Hydrogenation of the aqueous solution subsequent to decarbonylation further reduces organic impurities in dicarboxylic aromatic acid recovered by crystallization and separation from the aqueous solution. Such separation of purified solids from the aqueous mother liquor can, advantageously, be carried out under pressures near and/or at ambient pressures with consequent lower equipment and operating costs.

Processes according to this invention are particularly useful where the impure acid being purified is terephthalic acid formed by the oxidation of para-xylene, isophthalic acid formed by the oxidation of meta-xylene, or 2,6-naphthalene dicarboxylic acid formed by the oxidation of a 2,6-dialkylnaphthalene.

BACKGROUND OF THE INVENTION

Aromatic dicarboxylic acids are well known starting materials for making polyester resins, which polyester resins are used widely as principal polymers for polyester fibers, polyester films, and resins for bottles and like containers. For a polyester resin to have properties required in many of these uses, the polyester resin must be made from a polymer grade or "purified" aromatic acid. Polymer grade or purified terephthalic acid and isophthalic acid are the staring materials for polyethylene terephthalates and isophthalates, respectively, which are the principal polymers employed in the manufacture of polyester fibers, polyester films, and resins for bottles and like containers. Similarly, polymer grade or "purified" naphthalene dicarboxylic acids, especially 2,6-naphthalene dicarboxylic acid, are the starting materials for polyethylene naphthalates, which can also be employed in the manufacture of fibers, films and resins.

A purified terephthalic acid, isophthalic acid or naphthalene dicarboxylic acid can be derived from a relatively less pure, technical grade or "crude" terephthalic acid, isophthalic acid or "crude" naphthalene dicarboxylic acid, respectively, by purification of the crude acid utilizing hydrogen and a noble metal catalyst, as described for terephthalic acid in commonly assigned U.S. Pat. No. 3,584,039 to Meyer. In the purification process of Meyer, impure terephthalic acid, isophthalic acid or naphthalene dicarboxylic acid is dissolved in water or other suitable solvent or solvent mixture at an elevated temperature, and the resulting solution is hydrogenated, preferably in the presence of a hydrogenation catalyst, which conventionally is palladium on a carbon support, as described in commonly assigned U.S. Pat. No. 3,726,915 to Pohlmann. This hydrogenation step converts the various color bodies present in the relatively impure phthalic acid or naphthalene dicarboxylic acid to colorless products. Another related purification-by-hydrogenation process for aromatic polycarboxylic acids produced by liquid phase catalyst oxidation of polyalkyl aromatic hydrocarbons is described in commonly assigned U.S. Pat. No. 4,405,809 to Stech et al.

Terephthalic acid is, usually, produced by a liquid phase oxidation of para-xylene and/or para-toluic acid. Terephthalic acid is, previously noted, of great commercial importance and is widely used for the production of various different polymers, such as fiber-forming polyesters. A process for preparing polyesters of terephthalic acid, particularly polyethylene terephthalate, comprises a direct condensation of terephthalic acid with the respective poly-alcohol. For example, terephthalic acid is reacted with ethylene glycol to from bis(β-hydroxyethyl) terephthalate which is then polymerized in a subsequent stage. Direct condensation is simpler than other known methods such as transesterification of dimethyl terephthalate with the appropriate glycol. Direct esterification requires, however, use of medium or highly purified terephthalic acid. In order to be suitable for the production of polyester fibers, terephthalic acid must be substantially free of any contaminants which lower the melting point of the polyester and/or cause coloration of the polyester. Some impurities which are contained in crude terephthalic acid are, in fact, color-forming precursors.

All these impurities have not yet been identified. However, 4-carboxybenzaldehyde which is an intermediate oxidation product, is found in crude terephthalic acid. It is, likewise, known that the degree to which coloration in the polyester is induced is less if the 4-carboxybenzaldehyde content of the terephthalic acid is low. While pure 4-carboxybenzaldehyde itself does not necessarily promote coloring during polymerization, this impurity is a convenient tracer for evaluating the degree to which terephthalic acid has been refined. A process which can reduce the 4-carboxybenzaldehyde content of terephthalic acid reduces also the content of color-forming precursors.

Commercial crude terephthalic acid contains, typically, from about 800 to about 7,000 parts per million on a weight basis (ppm) 4-carboxybenzaldehyde and about 200 to 1,500 ppm para- toluic acid as the main impurities. Crude terephthalic acid also contains lesser amounts, for example in a range from about 20 to about 200 ppm, of yellow color aromatic compounds having the structures of benzil, fluorenone or anthraquinone which are characteristically yellow compounds as impurities resulting from coupling side reactions occurring during the oxidation of para-xylene.

U.S. Pat. No. 3,584,039 teaches a feasible, commercially useful method for purification of such commercially available crude terephthalic acid products by treating liquid phase solutions thereof in water at temperatures in a range from about 200° to about 374° C. with hydrogen in the presence of a solid hydrogenation catalyst (e.g. metallic palladium on carbon support) and crystallizing terephthalic acid from catalyst-free liquid phase solutions at temperatures in a range from about 50° C. to about 150° C. This catalytic hydrogen treatment converts, substantially, the 4-carboxybenzaldehyde to para- toluic acid and decolorizes the terephthalic acid.

British Patent Number 1,152,575 is directed to the development of the Meyer Patent method for its commercial application providing improved modes of conduct for the entire process from the step of dissolving crude terephthalic acid through the step of crystallizing terephthalic acid from the hydrogen treated aqueous solution. With respect to crystallization, the British patent teaches the use of solvent evaporation to effect the cooling necessary to precipitate crystalline terephthalic acid, but cautions that conduct of such evaporative cooling should avoid shock cooling of the solution as would occur by instantaneous flash evaporation of solvent because such shock cooling coprecipitates dissolved impurities which contaminate terephthalic acid product. To prevent the contaminating effect of such shock cooling, the British patent teaches that the evaporative cooling should be controlled by evaporation against equilibrium back pressure, for example, by throttling of steam vapor exhaust at the equilibrium pressure. This is in effect a controlled rate evaporative cooling.

Crystallization by controlled rate evaporative cooling is, according to the above British patent, applied to continuous crystallization conducted in three series connected stages under the conditions described to effect in 3.4 hours a 150° C. temperature drop from 277° C. initial solution temperature to the third stage temperature of 109° C. This mode of conducting the crystallization provided an average cooling rate of 1.48° F. per minute that was not only inordinately slow but, when applied to aqueous solutions of terephthalic acid of 2,400 ppm para-toluic acid content, also provided a terephthalic acid product containing 1,200 ppm para-toluic acid. Such product would not be acceptable for direct reaction with ethylene glycol for polyester fiber manufacture.

U.S. Pat. No. 3,452,088 repeats the caution against shock cooling and teaches a further improvement for the continuous controlled rate evaporative cooling technique as applied to crystallizing terephthalic acid from aqueous solutions also containing dissolved para-toluic acid. The improvement consists of limiting the final crystallization temperature and/or crystalline product separation temperature to the temperature range of 250° to 300° F. to prevent para-toluic acid contamination of crystallizing terephthalic acid. By using such final crystallization and/or product separation temperatures of 250° to 300° F. terephthalic acid could be and was commercially obtained with 150 ppm and less para-toluic acid from feed solutions containing 6,000 to 500 ppm para-toluic acid at a somewhat faster cooling rate of 3° to 4° F. per minute. But such faster controlled rate evaporation process does not provide a useful basis for devising still faster continuous flash evaporative crystallization to overcome the para-toluic acid contamination problem mentioned in both the British and U.S. patents.

Crystallization by flash evaporation of solvent has, in general, been long known and used to take advantage of the substantially instantaneous decrease in both temperature and pressure and attendant substantially instantaneous evaporation of solvent as the hot solution of solute is introduced into the crystallization vessel operated at a lower temperature and pressure. Advantageously, the rapidly vaporized portion of the liquid solvent flashed to the vapor phase permits rapid removal of solvent vapor. Both crystallization and crystal growth occur rapidly with the cooling and concentrating caused by flashing the solution to the lower temperature. Growth of crystals is, substantially, entirely at the lower temperature and is independent of residence time. Crystal size in a crystallization vessel where solvent is flash evaporated can, as is well known, be enhanced by circulation of slurry of crystals throughout the lower portion of the crystallization vessel. For example, one means for accomplishing such circulation in a stirred crystallization zone is to withdraw a portion of the slurry from near its upper level and introduce, e.g., by pumping, the withdrawn slurry up through the bottom of the stirred slurry.

Use of flash solvent evaporation induced crystallization of terephthalic acid from aqueous solution also containing dissolved para-toluic acid in amounts of about 500 to about 6,000 ppm based on terephthalic acid can, without proper conduct thereof, bring into play the para-toluic acid contamination phenomenon alluded to in the British patent and more generally described in the later U.S. patent. Such contamination phenomenon is somewhat anomalous because, in spite of the fact that there is retained more than enough solvent water to prevent saturation or supersaturation with respect to para-toluic acid, para-toluic acid nevertheless comes out of solution. The later U.S. patent suggests that the contamination phenomenon is in some way dependent on the rate of crystallization and the final temperature of crystallization and product separation and not solely on para-toluic acid concentration in the solution.

From plots of terephthalic acid saturation and supersaturation (terephthalic acid concentrations vs. temperature) and guidance provided by teachings in the aforementioned related British and United States patents, one might devise a continuous terephthalic acid crystallization process having a number of crystallization stages in series with each stage operated at a temperature lower than the preceding stage and, for smooth operation approximating batchwise crystallization, having a temperature profile substantially following the terephthalic acid saturation plot. Such a devised continuous crystallization process would have at least about 40 rate dependent crystallization stages. However, because of the number of stages and their time consuming operation, such a continuous crystallization would not be economically attractive or feasible for commercial application.

Puskas et al., in commonly assigned U.S. Pat. Nos. 4,394,299 and 4,467,110 disclose the use of a combination noble metal catalyst, for example, a palladium/rhodium catalyst on a porous carbonaceous surface, for Hydrogenation of aqueous terephthalic acid solutions. These two patents also show the use of a rhodium-on-carbon catalyst under reducing conditions and review various heretofore known methods of preparing a Group VIII metal catalyst having activity and selectivity suitable for the purification of terephthalic acid by hydrogenating its principal impurity, 4-carboxybenzaldehyde, to para-toluic acid.

However, para-toluic acid is also an impurity that must be removed from the hydrogenated aqueous terephthalic solution. While such removal can be achieved to a large extent owing to somewhat the greater solubility of para-toluic acid as compared to terephthalic acid in water, nevertheless, substantial amounts of para-toluic acid are trapped within purified terephthalic acid crystals as the hydrogenated terephthalic acid solution is crystallized to recover purified terephthalic acid.

Recently, in commonly assigned U.S. Pat. No. 5,175,355 to Streich et al., a method is disclosed for recovery of purified terephthalic acid using rotary pressure filtration apparatus which is commercially available. After purification of crude terephthalic acid in the presence of water, wherein 4-carboxybenzaldehyde is, substantially, hydrogenated to para-toluic acid, and terephthalic acid is carefully crystallized to limit co-crystallization of para-toluic acid, purified terephthalic acid is recovered from its aqueous mother liquor solution in a rotary pressure filter having a plurality of filter cells. The rotary pressure filter employed is adapted so that filter cake of purified terephthalic acid in each filter cell is washed with water to remove residual soluble para-toluic acid. After this washing with water under pressures in a range upward from about 40 psig to about 65 psig, the filter cake is, optionally, discharged from the pressure filter to ambient pressures. The Streich et al. process for flooded water washing of filter cake under elevated pressure substitutes the pressure centrifugation, reslurry, atmospheric pressure flashing and atmospheric pressure separation steps utilized in prior art processes to recover purified terephthalic acid from an aqueous slurry by a rotary pressure filter, e.g., by using a BHS-FEST (TM) rotary pressure filtration apparatus.

To avoid disadvantages attendant to the separation of para-toluic acid from the terephthalic acid crystals, it has been proposed to decarbonylate 4-carboxybenzaldehyde in aqueous solutions to benzoic acid in the presence of a palladium-on-carbon catalyst but without the simultaneous hydrogenation of the other impurities that may be present in aqueous solutions of crude terephthalic acid since benzoic acid is more soluble in water then para-toluic acid. See, for example, commonly assigned U.S. Pat. No. 3,456,001 to Olsen. This proposed decarbonylation of 4-carboxybenzaldehyde to benzoic acid produces, however, equimolar amounts of carbon monoxide, a well-known poison for the noble metals such as palladium.

Kimura et al., U.S. Pat. No. 4,201,872, describes using a catalyst of palladium supported on active carbon to effect decarbonylation of the 4-carboxybenzaldehyde impurity in crude terephthalic acid obtained by liquid phase oxidation of para-xylene in water at high temperature under high pressure. Carbon monoxide, which is formed by decarbonylation of the 4-carboxybenzaldehyde and dissolved in the liquid phase, was found to poison the catalyst of palladium supported on active carbon which resulted in a decrease in catalyst activity for the decarbonylation of 4-carboxybenzaldehyde. In an attempt to minimize catalyst poisoning, Kimura et al. propose to carry out the decarbonylation at relatively low process pressures so as to minimize dissolved carbon monoxide concentration in the liquid reaction medium. According to Kimura et al., carbon monoxide dissolved in the liquid phase can be removed from the liquid phase to a gaseous phase by decreasing the pressure over the catalyst bed in the decarbonylation step thereby prolonging the lifetime of the catalyst. The generated carbon monoxide is purged from the reactor as a gas.

Kimura et al. describe a process consisting essentially of contacting an aqueous solution of crude terephthalic acid obtained from the oxidation step with a catalyst of palladium supported on active carbon to effect decarbonylation under a limited pressure of an ambient atmosphere comprising steam and carbon monoxide; and cooling the solution to effect separation by crystallization of pure terephthalic acid from solution thereby leaving water soluble impurities comprising benzoic acid formed by decarbonylation in solution. The amount of carbon monoxide present is only that amount derived by the decarbonylation of the 4-carboxybenzaldehyde. Process pressures also must be controlled within a closely defined pressure range. The limited pressure is in a range from the vapor pressure ($kg/cm^2$) of the aqueous solution at the reaction temperature of 200° C. to 320° C., up to pressure equal to the sum of said vapor pressure with no more additional pressure than 5 $kg/cm^2$ or, optionally, with additional pressure of only 3 $kg/cm^2$. U.S. Pat. No. 4,201,872 contains no mention of titanium dioxide-supported purification catalysts or of hydrogenation prior to recovery of terephthalic acid by crystallization.

Japanese Patent Application Number 145922/76 describes using a catalyst of Group VIII metals and/or their oxides for purification of aromatic dicarboxylic acids in a process step characterized by passing aqueous solutions of crude aromatic dicarboxylic acid through a bed of catalyst which was not allowed to come into contact with molecular hydrogen, and another process step of allowing the solution to contact catalyst and molecular hydrogen. In an attempt to minimize catalyst poisoning, applicants propose that deactivated catalyst of palladium impregnated activated carbon, i.e., catalyst which lost hydrogen-addition activity by having been used in the purification of terephthalic acid by hydrogen addition, should be suitable for the first process step. Japanese Patent Application Number 145922/76 contains no mention of any titanium dioxide-supported purification catalyst.

Carbon is conventionally used as the support material for the noble metal in the catalyst employed in the aforesaid purification processes. A common disadvantage of the use of a carbon support is that carbon fines are often generated during commercial operations. The generation of such fines can be minimized but generally cannot be completely avoided. During the subsequent esterification process, such particulates introduced with the particular purified acid, for example, terephthalic acid, isophthalic acid or 2,6-naphthalene dicarboxylic acid, can plug filters and thereby cause interruptions in the process. Other such particulates that bypass the filter may be incorporated into the resulting polyester fiber or film and cause fiber breakage or film distortion.

For this reason, it is highly desirable to use other materials as the support material in the catalyst employed in the aforesaid purification method. However, because of the highly corrosive conditions under which the aforesaid purification is performed, it has proven difficult to develop suitable non-carbon catalyst supports for use in the purification catalyst. For example, as indicated in Meyer, U.S. Pat. No. 3,594,039 in column 5, lines 10 to 14, hot aqueous solutions of terephthalic acid dissolve supporting materials such as natural and synthetic alumina, silica, silica-alumina, kieselguhr, calcined clays, zirconium supports and other metal oxides and metal salt containing supports.

M. Bankmann, R. Brand, B. H. Engler and J. Ohmer, "Forming of High Surface Area $TiO_2$ to Catalyst Supports," *Catalysis Today*, Vol. 14, pages 225–242 (1992), contains an extensive discussion of the use of titanium dioxide having a high surface area as a catalyst support. The article (which was previously presented in a substantially identical form by R. Brand at the Fall, 1991, American Chemical Society meeting) indicates that the titanium dioxide must have a high surface area in order to be a suitable catalyst support and discusses only titanium dioxide having surface areas of 50 and 100 square meters per gram. The article discusses the extrusion process for manufacturing titanium dioxide having the requisite high surface area and the effect of the raw materials, additives and process parameters employed in the extrusion process on catalytically important characteristics of the resulting titanium dioxide. As disclosed, the extrusion process involves the steps of (1) mixing and kneading the raw materials, (2) extruding, (3) drying, and (4) calcining, each of which influences the quality of the resulting support. Correlations between the concentration of water, plasticizers and binders and the type of titanium dioxide raw material employed in the mixing and kneading step and the crushing strength, attrition resistance, pore diameter and pore volume of the resulting catalyst support, and correlations between the calcination temperature and the surface area, pore volume, mean pore diameter and pore size distribution and the degree of transformation from the anatase crystalline phase to the rutile crystalline phase in the resulting catalyst support, are discussed in the article. More particularly, the use of catalysts containing palladium, platinum or rhodium components supported on titanium dioxide for selective hydrogenation is disclosed. On pages 240 to 241, the use of such catalysts to hydrogenate a para-substituted benzaldehyde to the corresponding para-substituted benzyl alcohol or para-substituted toluene is disclosed. The table on page 241 indicates that the para-substituent can be a carboxylic acid group, a methyl group or a halogen. The article discloses that the results of the hydrogenation of para-substituted benzaldehyde were substantially different depending upon whether the catalyst contained palladium, platinum or rhodium on the titanium dioxide support. The article indicates that the titanium dioxide must have a high surface area in order to be a suitable catalyst support and discusses only titanium dioxide having surface area of 50 and 100 square meters per gram. In addition, the article discloses that depending on the reaction temperature employed, the reduction of a para-substituted benzaldehyde affords either of several products with high selectivity and in high yield. Except for the catalysis, the reaction temperature and the hydrogen pressure employed, the article does not disclose the conditions under which the hydrogenation was performed.

Commonly assigned U.S. Pat. No. 4,743,577 to Schroeder et al. discloses that the use of catalysts containing palladium finely dispersed on carbon in the aforesaid purification-by-hydrogenation of terephthalic acid derived from the oxidation para-xylene results in contamination of the resulting purified terephthalic acid with fines produced by abrasion of the carbon granulates due to their relatively low crush strength and abrasion resistance. This patent discloses that reduced fines contamination results from the use instead of a catalyst containing a thin layer of palladium, nickel, rhodium, platinum, copper, ruthenium and cobalt on a porous sintered support of metallic titanium, zirconium, tungsten, chromium, nickel, and alloys incorporating one or more of these metals. The surface area of palladium-plated supports of titanium, Inconel and nickel are disclosed as 0.22, 0.55 and 1.21 square meters per gram, respectively, which are very significantly smaller than smaller surface area of a palladium on active carbon catalyst.

Commonly assigned U.S. Pat. No. 5,292,934 to Sikkenga et al. discloses the preparation of an aromatic carboxylic acid by the liquid phase catalyzed oxidation of an alkyl-substituted aromatic compound such as 2,6-dimethylnaphthalene, ortho-xylene, meta-xylene, or para-xylene. The U.S. Pat. No. 5,292,934 further discloses that the resulting aromatic dicarboxylic acids can be purified by hydrogenation thereof in the presence of a catalyst comprising one or more Group VIII metals deposited on a support such as alumina, titania or carbon The application contains no other mention of titania.

Timruer et al., U.S. Pat. No. 4,831,008, describes using a catalyst containing a rhodium-containing component supported on titanium dioxide for the hydrogenation of benzene, toluene, ortho-xylene, terephthalic acid, disodium terephthalate, and diethyl terephthalate, in which the aromatic ring is hydrogenated.

Commonly assigned U.S. Pat. No. 4,892,972 to Schroeder et al. discloses that aqueous solutions of crude terephthalic acid can be purified by hydrogenation in the presence of plural noble metal catalysts in separate layers. Initially, the solution to be purified is passed through a layer of ruthenium-on-carbon catalyst, rhodium-on-carbon catalyst, or platinum-on-carbon catalyst, and thereafter through a layer of palladium-on-carbon catalyst, both under reducing conditions, i.e., while in the presence of hydrogen. Hydrogenation in the presence of plural noble metal catalysts in separate layers according to U.S. Pat. No. 4,892,972 involves conversion of 4-carboxybenzaldehyde to para-hydroxy-methyl-benzoic acid and/or to para-toluic acid and substantial conversion of 4-carboxybenzaldehyde to benzoic acid concurrently with a Fischer-Tropsch type of reaction in the same reaction vessel which converts generated carbon monoxide to a hydrocarbon moiety such as methane, ethane, or the like. Decarbonylation and carbon monoxide conversions to a hydrocarbon moiety are believed to occur substantially simultaneously in the first layer of the layered fixed catalyst bed of this invention. Such carbon monoxide conversions also require hydrogen. Thus the amount of molecular hydrogen supplied to the liquid-filled particulate bed is at least equal to (i) that stoichiometrically required to effect hydrogenation of a portion of the 4-carboxybenzaldehyde content of the aqueous solution to form para-hydroxymethyl-benzoic acid and/or para-toluic acid and (ii) that stoichiometrically required to form hydrocarbon moieties from a major portion of the carbon monoxide generated by decarbonylation to benzoic acid of another portion of the 4-carboxybenzaldehyde. The patent contains no mention of employing a noble metal supported on a carrier comprising titanium dioxide.

Recently, in commonly assigned U.S. Pat. No. 5,362,908 to Schroeder et al., a method employing a titanium dioxide-supported purification catalyst is disclosed for purification-by-hydrogenation of a crude terephthalic acid, crude isophthalic acid or a crude naphthalene dicarboxylic acid produced by the liquid-phase oxidation with an oxygen-containing gas in a solvent at an elevated temperature and pressure and in the presence of an oxidation catalyst comprising a heavy metal component. The purification-by-hydrogenation process according to U.S. Pat. No. 5,362,908 comprises passing an at least partially aqueous solution of crude aromatic dicarboxylic acid at a pressure sufficient to maintain the solution substantially in the liquid phase through a particulate catalyst bed in the presence of hydrogen. Particulate catalyst for this purification-by-hydrogenation process is a noble metal of Group VIII of the Periodic Table of Elements on a titanium dioxide support which does not disintegrate in less than one month under conditions employed in the hydrogenation. Preferably, at least one weight percent of the titanium dioxide support is in the rutile crystalline phase, and at least about 90 weight percent of the titanium support is, more preferably, in the rutile crystalline phase. The patent contains no mention of employing a noble metal supported on a carrier comprising titanium dioxide under conditions suitable for decarbonylation of organic impurities.

However, even after hydrogenation, the terephthalic acid product contains color bodies. It is highly desirable to reduce the concentration of such color bodies that remain in purified terephthalic acid. The color level of purified terephthalic acid product is generally measured directly either by measuring the optical density of solutions of purified terephthalic acid or the b*-value of the solid purified terephthalic acid itself. Optical density of purified terephthalic acid is measured as the absorbency of light at 340 nanometers in its basic solution, i.e., in a solvent such as sodium hydroxide or ammonium hydroxide.

Furthermore, even after hydrogenation, the terephthalic acid product often contains impurities which fluoresce at wavelengths of 3 nanometers upon excitation at wavelengths of 260–320 nanometers. Further reduction of such fluorescence of the purified terephthalic acid product is highly desirable. Since the concentration of such impurities in purified terephthalic acid can vary significantly, specifications are often established for the amount of such fluorescence which can be permitted for the purified terephthalic acid product. The problem of the control of such fluorescence by purified terephthalic acid is complicated because some of the fluorescent impurities are soluble and can be removed by conventional procedures for purifying terephthalic acid while other such fluorescent impurities are insoluble and cannot be removed by such conventional procedures. Upon chemical reduction during purification of crude terephthalic acid, some impurities which do not themselves fluoresce at wavelengths of 39 nanometers upon excitation at wavelengths of 260–320 nanometers are converted to their reduced forms which fluoresce at 39 nanometers upon excitation by wavelengths of 260–320 nanometers.

Regardless of the dicarboxylic aromatic acid desired, there is a need for improved catalytic processes for economical purification of relatively impure dicarboxylic aromatic acid produced by liquid-phase oxidation of a suitable benzene or naphthalene. Processes which can demonstrate treatment of higher levels of impurities without loss in quality of purified acid product should be very useful. Improvements which extend useful catalyst life could provide more economical purification processes. A catalytic process which extends useful catalyst life while treating crude acid having higher levels of impurities and provides improvements in quality of the purified acid product would be particularly advantageous.

It is therefore a general object of the present invention to provide an improved process which overcomes the aforesaid problem of prior art methods, for production of purified aromatic acids from liquid phase oxidation which can be used for manufacture of polyester fibers, polyester films, and resins in bottles and like containers.

More particularly, it is an object of the present invention to provide an improved method for production of purified aromatic acid sufficiently free of undesired impurities so that the acid can be used to make polyester resins which have good color and other properties needed in manufacture of commercial articles.

It is therefore a general object of the present invention to provide an improved method which overcomes the aforesaid problems of prior art methods, for purifying a crude phthalic acid or crude naphthalene dicarboxylic acid produced by the liquid-phase oxidation of ortho-xylene, meta-xylene, or para-xylene or a dialkylnaphthalene, respectively, with an oxygen-containing gas in a solvent and in the presence of an oxidation catalyst.

More particularly, it is an object of the present invention to provide an improved aforesaid purification method that employs a catalyst which does not produce particulates during the purification operation and yet has a high catalytic activity and lifetime.

It is another object of the present invention to provide an improved aforesaid purification method that employs a catalyst that, even after a substantial period of aging, reduces the amounts of 4-carboxybenzaldehyde to substantially lower levels.

It is further an object of this invention to provide an improved process for preparation of purified terephthalic acid wherein purified terephthalic acid product is recovered from its mother liquor while maintaining temperatures within a range downward from about 100° C. to about 25° C. and the purified terephthalic acid is near or at atmospheric pressure, and is thereby in a state to be processed by a dryer at atmospheric pressure.

Other objects and advantages of the invention will become apparent upon reading the following detailed description and appended claims.

SUMMARY OF THE INVENTION

Economical processes are disclosed for purification of a relatively impure dicarboxylic aromatic acid. Processes of this invention comprise passing an aqueous solution of dicarboxylic aromatic acid with small amounts of organic impurities consisting of oxygen-containing aromatic co-products of oxidation and/or other organic components, through a particulate bed of purification catalyst comprising at least one noble metal supported on a carrier comprising titanium dioxide under conditions suitable for decarbonylation of organic impurities. Generally, at least one weight percent of the titanium dioxide support is in the rutile crystalline phase. Advantageously, the titanium dioxide support has at least about 90 weight percent of the titanium support in the rutile crystalline phase.

More particularly, the present invention is a process for purification of a relatively impure dicarboxylic aromatic acid produced by liquid-phase oxidation of a corresponding benzene having two oxidizable alkyl or acyl ring substituents or an oxidizable alkyl and acyl ring substituent in non-adjacent positions or a corresponding naphthalene having two oxidizable alkyl or acyl ring substituents or oxidizable alkyl and acyl ring substituent, with a dioxygen-containing gas in a solvent at an elevated temperature and pressure and in the presence of an oxidation catalyst comprising a heavy metal component, and/or hydrolysis of polyester resin comprising repeating units of aromatic acid residue and repeating units of dihydric alcohol residue linked by ester bonds. The purification process comprises; passing an at least partially aqueous solution of from about 5 to about 50 weight percent of the impure dicarboxylic aromatic acid at a temperature of from about 100° C. to about 350° C. and at a pressure of at least 5.5 kg/cm² above the pressure sufficient to maintain the solution substantially in the liquid phase, through a particulate bed of purification catalyst comprising a noble metal of Group VIII of the Periodic Table of Elements on a titanium dioxide support which does not disintegrate in less than one month under the aforesaid conditions employed in the purification, and in the presence of at most an amount of hydrogen formed by chemical conversions within the catalyst bed, and thereafter cooling the aqueous solution to effect separation of relatively pure dicarboxylic aromatic acid from the aqueous solution by crystallization.

Where aromatic acid product of higher purity is desired, processes for purifying dicarboxylic aromatic acid according to this invention, further comprises: reducing at least a portion of the organic impurities in the crude dicarboxylic aromatic acid in an aqueous solution at elevated temperatures and pressures and in the presence of hydrogen and at least one insoluble Group VIII noble metal-containing catalyst; separating the aqueous solution from the solid noble metal-containing catalyst; and thereafter crystallizing and separating purified dicarboxylic aromatic acid from the aqueous solution while maintaining temperatures suitable for the desired separation.

Separation of relatively pure dicarboxylic aromatic acid from aqueous solution is, generally, carried out by crystallization at temperatures in a range upward from about 25° C. to about 200° C. or even higher a temperature. Separation of purified terephthalic acid from its mother liquor is, advantageously, effected while maintaining temperatures within a range downward from about 100° C. to about 25° C., preferably while maintaining temperatures within and below the range of from about 100° C. to about 75° C., more preferably while maintaining temperatures within and below the range of from about 100° C. to about 85° C. Crystallization and separation of purified naphthalene dicarboxylic acid from the aqueous solution is, generally, effected while maintaining temperatures in a range downward from about 175° C., preferably while maintaining temperatures within and below the range of from about 150° C. to about 25° C.

In one embodiment of this invention, dicarboxylic aromatic acid is purified by a process which comprises: (i) passing an at least partially aqueous solution of from about 5 to about 50 weight percent of the impure dicarboxylic aromatic acid at a temperature of from about 100° C. to about 350° C. and at a pressure of at least 5.5 kg/cm² above the pressure sufficient to maintain the solution substantially in the liquid phase, through an initial particulate bed of purification catalyst comprising a noble metal of Group VIII of the Periodic Table of Elements on a titanium dioxide support having at least one weight percent of the titanium dioxide support in the rutile crystalline phase, and in the presence of at most an amount of hydrogen formed by chemical conversions within the initial catalyst bed; (ii) passing effluent aqueous solution from the initial bed at a temperature of from about 100° C. to about 350° C. and at a pressure sufficient to maintain the solution substantially in the liquid phase, through a subsequent particulate bed of another purification catalyst and in the presence of a molecular hydrogen-containing gas, wherein the subsequent bed of catalyst comprises a noble metal of Group VIII of the Periodic Table of Elements supported on an active carbon carrier; (iii) cooling the aqueous solution to effect separation of purified dicarboxylic aromatic acid from a resulting mother liquor by crystallization; and (iv) thereafter recovering purified dicarboxylic aromatic acid product from the resulting mother liquor while maintaining temperatures within a range downward from about 100° C. to about 25° C.

Another embodiment of this invention is a process for purification of a relatively impure terephthalic acid produced by oxidation in the liquid phase of para-xylene with a dioxygen-containing gas at temperatures in a range of from about 120° C. to about 240° C. in the presence of an oxidation catalyst comprising cobalt, manganese, and bromine components, and in a solvent system comprising a $C_1$ to $C_6$ monocarboxylic aliphatic acid, the solvent system containing from 1 weight percent to 20 weight percent of water. The resulting product is a solution of relatively impure or crude terephthalic acid that includes relatively large amounts of impurities, such as 4-carboxybenzaldehyde which can be present in amounts up to about 10,000 parts per million of terephthalic acid by weight. These impurities adversely affect terephthalic acid polymerization reactions to produce polyethylene terephthalate as well as cause undesirable coloring of the resulting polyethylene terephthalate polymers.

Purification of such impure terephthalic acid according to the present invention comprises: (i) passing an at least partially aqueous solution of from about 5 to about 50 weight percent of the impure terephthalic acid at a temperature of from about 100° C. to about 350° C. and at a pressure of at least 5.5 kg/cm², preferably in a range upward from about 6 kg/cm², more preferably in a range upward from about 7 kg/cm², above the pressure sufficient to maintain the solution substantially in the liquid phase, through an initial particulate bed of purification catalyst comprising a noble metal of Group VIII of the Periodic Table of Elements on a titanium dioxide support which does not disintegrate in less than one month under the aforesaid conditions employed in the purification, preferably on a titanium dioxide support having at least one weight percent of the titanium dioxide support in the rutile crystalline phase, and in the presence of at most an amount of hydrogen formed by chemical conversions within the initial catalyst bed; (ii) passing effluent aqueous solution from the initial bed through a subsequent particulate bed of purification catalyst comprising at least palladium supported on an active carbon carrier at temperatures in a range of from about 245° C. to about 300° C. and pressures sufficient to maintain the solution substantially in the liquid phase, and in the presence of a molecular hydrogen-containing gas, at space velocities of the aqueous solution through the subsequent bed of particulate catalyst in a range of from about 5 hours$^{-1}$ to about 25 hours$^{-1}$, preferably in a range of from about 10 hours$^{-1}$ to about 15 hours$^{-1}$; (iii) cooling the aqueous solution to effect separation of purified dicarboxylic aromatic acid from a resulting mother liquor by crystallization; and (iv) recovering, thereafter, purified dicarboxylic aromatic acid product from the resulting mother liquor while maintaining temperatures within a range downward from about 100° C. to about 25° C., preferably while maintaining temperatures within and below the range of from about 100° C. to about 75° C., more preferable while maintaining temperatures within and below the range of from about 100° C. to about 85° C.

Fiber-grade terephthalic acid is, generally, obtained using a hydrogenation catalyst in which the noble metal is at least one member of the group consisting of palladium and rhodium. Purified terephthalic acid produced according to this invention has a total metals content of less than 100 ppm and contains less than 1000 ppm total of 4-carboxybenzaldehyde and para-toluic acid.

When the insoluble metal-containing catalyst has a palladium containing component on a carbon support, terephthalic acid produced from waste polyethylene terephthalate according to this invention has a total metals content of less than 10 ppm, and color measured by a L*-value greater than about 95, preferably in a range of from about 95 to about 100, an a*-value greater than about −1.5, preferably in a range of from about −1 to about +1, and a b*-value less than about 2, preferably in a range of from about 0.5 to about 2.

Yet another embodiment of this invention is a process for purification of a relatively impure 2,6-naphthalene dicarboxylic acid formed by the oxidation of a 2,6-dialkylnaphthalene with a dioxygen-containing gas carried out at temperatures in a range of from about 120° C. to about 240° C. in the presence of an oxidation catalyst comprising cobalt, manganese, and bromine components in a solvent system comprising acetic acid containing from 1 weight percent to 20 weight percent of water in the liquid phase, which purification comprises: (i) passing an at least partially aqueous solution of from about 5 to about 50 weight percent of the impure 2,6-naphthalene dicarboxylic acid at a temperature of from about 100° C. to about 350° C. and at a pressure of at least 7 kg/cm² above the pressure sufficient to maintain the solution substantially in the liquid phase, through an initial particulate bed of purification catalyst comprising a noble metal of Group VIII of the Periodic Table of Elements on a titanium dioxide support having at least one weight percent of the titanium dioxide support in the rutile crystalline phase, and in the presence of at most an amount of hydrogen formed by chemical conversions within the initial catalyst bed; (ii) passing effluent aqueous solution from the initial bed through a subsequent particulate bed of purification catalyst comprising at least palladium supported on an active carbon carrier at temperatures of from about 245° C. to about 300° C. and pressures sufficient to maintain the solution substantially in the liquid phase, and in the presence of a molecular hydrogen-containing gas, at space velocities of the aqueous solution through the subsequent bed of particulate catalyst in a range of from about 10 hours⁻¹ to about 15 hours⁻¹; and (iii) thereafter crystallizing and separating purified 2,6-naphthalene dicarboxylic acid from the aqueous solution while maintaining temperatures in a range of from about 25° C. to about 150° C.

A preferred processes for obtaining purified 2,6-naphthalene dicarboxylic acid further comprises: reducing at least a portion of the organic impurities in the crude 2,6-naphthalene dicarboxylic acid in an aqueous solution at elevated temperatures and pressures and in the presence of hydrogen and at least one insoluble Group VIII noble metal-containing catalyst; separating the solid noble metal-containing catalyst from the aqueous solution; and crystallizing and separating from the aqueous solution purified 2,6-naphthalene dicarboxylic acid having an optical density in a range from about 0 to about 5, an ash content of less 20,000 ppm, and/or a metals content of less than 20,000 ppm, while maintaining the temperature in a range of from about 25° C. to about 150° C.

BRIEF DESCRIPTION OF THE INVENTION

Processes of this invention are particularly suitable for use in purification of relatively impure dicarboxylic aromatic acids, particularly crude phthalic and naphthalene dicarboxylic acids. Generally, the impure dicarboxylic acid is a crude product of catalytic, liquid-phase oxidation of a benzene having two oxidizable alkyl or acyl ring substituents or an oxidizable alkyl and acyl ring substituent in the meta or para positions, i.e. non-adjacent, or naphthalene having two oxidizable alkyl or acyl ring substituents or an oxidizable alkyl and acyl ring substituents, but can also be crude acid product recovered from waste polyester resins comprising repeating units of the dicarboxylic aromatic acid residue and repeating units of dihydric alcohol residue.

Suitable alkyl groups contain from 1 to 6 carbon atoms, and suitable acyls also contain from 1 to 6 carbon atoms. Examples of suitable naphthalene-based aromatic feed compounds include; 1,2-dimethylnaphthalene, 2,6-dialkylnaphthalene or 2-acyl-6-alkyl naphthalene, 2,6-dimethyl-, 2,6-diethyl- or 2,6-diisopropyl-, 2-acetyl-6-methyl- and 2-methyl-6-ethyl naphthalene. The crude acid being purified preferably is either terephthalic acid formed by the oxidation of para-xylene, isophthalic acid formed by the oxidation of meta-xylene or 2,6-naphthalene dicarboxylic acid formed by the oxidation of 2,6-dialkylnaphthalene (preferably 2,6-dimethyl naphthalene), and more preferably is terephthalic acid formed by the oxidation of para-xylene. It is of course understood that, prior to being purified, the crude acid, for example, 2,6-naphthalene dicarboxylic acid, can have been previously esterified to form the ester, for example, dimethyl naphthalene dicarboxylate, and then hydrolyzed to form the acid which is then purified by the method of this invention.

Suitable solvents for use in liquid phase oxidation method for producing crude acid to be purified by processes of this invention include water and any aliphatic $C_2$ to $C_6$ monocarboxylic acid such as acetic acid, propionic acid, n-butyric acid, isobutyric acid, n-valeric acid, trimethylacetic acid and caproic acid, and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude acid product from the product stream, at least a portion of the mother liquor (solvent) in the resulting product stream is generally recycled to the reactor.

Source of molecular oxygen employed in the liquid phase oxidation method for producing the crude phthalic acid or crude naphthalene dicarboxylic acid product to be purified by processes of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl substituent of the meta-xylene, para-xylene or dimethylnaphthalene being oxidized will provide such 0.5 to 8 volume percent of oxygen (measured on a solvent-free basis) in the gas-vapor mixture in the vapor condenser.

Catalyst employed in liquid phase oxidation method for producing crude terephthalic acid, isophthalic acid or a crude naphthalene dicarboxylic acid product comprises a heavy metal component, and can additionally comprise promoters or accelerators known in the art. In general, suitable heavy metal oxidation catalysts include those metals having an atomic number of about 21 to about 82, inclusive. A promoter such as a suitable source of bromide, a low molecular weight ketone having from 2 to 6 carbon atoms or a low molecular weight aldehyde having 1 to 6 carbon atoms can be used. The catalyst preferably comprises cobalt, more preferably comprises cobalt, and manganese-containing components, and most preferably comprises cobalt, manganese, and bromine-containing components. The weight ratio of cobalt (calculated as elemental cobalt) in the cobalt component of the polyalkyl aromatic compounds in the liquid-phase oxidation is in the range of from about 0.2 to about 10 milligram atoms (mga) per gram mole of polyalkyl aromatic. The weight ratio of manganese, calculated as elemental manganese, in the manganese component of the catalyst-to-cobalt, calculated as elemental cobalt, in the cobalt component of the catalyst in the liquid-phase oxidation is in a range of from about 0.2 to about 10 mga per mga of cobalt. The weight ratio of bromine, calculated as elemental bromine, in the bromine component of the catalyst-to-total cobalt and manganese, calculated as elemental cobalt and elemental manganese, in the cobalt and manganese components of the catalyst in the liquid-phase oxidation is in a range of from about 0.2 to about 1.5 mga per mga of total cobalt and manganese (toga).

Each of the cobalt and manganese components can be provided in any of its known ionic or combined forms that provide reactive forms of cobalt, manganese, and bromine in the solvent in the reactor. For example, when the solvent is an acetic acid medium, cobalt and/or manganese carbonate, acetate, tetra hydrate, and/or bromine can be employed. The 0.2:1.0 to 1.5:1.0 bromine to total cobalt and manganese milligram atom ratio is provided by suitable source of bromine. Such bromine sources include elemental bromine ($Br_2$), or ionic bromine (e.g., HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylenedibromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

In operation, minimum pressure at which the oxidation reactor is maintained is that pressure which will maintain a substantial liquid phase of the polyalkyl aromatic compounds and at least 70 percent of the solvent. Polyalkyl aromatic compounds and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in a range of from about 0 $kg/cm^2$ to about 35 $kg/cm^2$, and typically are in a range of from about 5 $kg/cm^2$ to about 30 $kg/cm^2$. Temperatures within the oxidation reactor range, generally, from about 120° C., preferably from about 150° C., to about 240° C., preferably to about 230° C. Residence time of solvent in the oxidation reactor is generally from about 20 to about 150 minutes and preferably from about 30 to about 120 minutes.

Liquid phase oxidation can be performed either in a batch, continuous or semi-continuous mode. In the batch mode, substituted benzene or naphthalene to be oxidized, solvent and catalyst components are initially introduced batchwise into a reactor, and the temperature and pressure of the reactor contents are then raised to the desired levels for the commencement of the oxidation reaction. Air is introduced continuously into the reactor. After commencement of the oxidation reaction, for example, after all of the substituted benzene or naphthalene to be oxidized has been completely introduced into the reactor, the temperature of the reactor contents is raised. In the continuous mode, each of the aforesaid substituted benzene or naphthalene to be oxidized, air, solvent, and catalyst are continuously introduced into the oxidation reactor, and a product stream comprising the resulting crude acid oxidation product and catalyst components dissolved in the solvent is withdrawn from the reactor. In the continuous mode solvent and catalyst are initially introduced into the reactor and then substituted benzene or naphthalene to be oxidized and air are continuously introduced into the reactor.

For large-scale commercial operation, it is preferable to use a continuous oxidation process. In such a process the weight ratio of monocarboxylic acid solvent to the aromatic feed to be oxidized is preferably about 2:1 to about 12:1, the toga ratio of manganese to cobalt is about 15:1 to about 0.3:1, the toga ratio of bromine to the total of cobalt and manganese is about 0:3:1 to about 0.8:1, and the total of cobalt and manganese, calculated as elemental cobalt and elemental manganese is at least about 0.40 weight percent based on the weigh of the solvent, and the oxidation reaction temperature is about 185° C. to about 250° C. Acetic acid is the most suitable solvent for such preferred continuous oxidation.

Depending on aromatic feed compound oxidized, components of catalyst selected and levels of catalyst components selected, and oxidation reaction conditions used, the reaction mixture produced in the oxidation reaction contains, in addition to the desired aromatic carboxylic acid, a number of impurities and reaction co-products. For example, terephthalic acid impurities are of several types. The compound 4-carboxybenzaldehyde, an intermediate product in the oxidation of para-xylene, is found in impure terephthalic acid. Unidentified color-forming precursors and color bodies, possibly of the benzil, fluorenone or anthraquinone structure, are also usually present.

When 2,6-dimethylnaphthalene is the aromatic feed compound for the oxidation reaction and a catalyst comprising cobalt, manganese and bromine components is used, the oxidation reaction mixture directly from the oxidation reactor (also called the total reactor effluent or TRE) contains the reaction solvent, which is typically a mixture of acetic acid and water, the desired 2,6-naphthalene dicarboxylic acid, and impurities including trimellitic acid, bromo-2,6-naphthalene dicarboxylic acid, 2-formyl-6-naphthoic acid, 2-naphthoic acid, a collection of other impurities, and cobalt and manganese catalyst components. The acetic acid and water can be removed by evaporation or distillation from the oxidation reaction mixture to leave a residue of solids. Analysis of these solids provides a useful assessment of all of the solid components in the oxidation reaction mixture and consequently an assessment of the yield of desired product and reaction by-products. In a typical oxidation of 2,6-dimethyl naphthalene, the amount of trimellitic acid in the oxidation reaction mixture solids can be as high as 5 weight percent of the solids and typically about 3 to about 4 weight percent. The amount of 2-formyl-6-naphthoic acid can be as high as 1 weight percent and typically is about 0.4 to about 0.5 weight percent. The amount of bromo-2,6-naphthalene dicarboxylic acids can be as high a 3 weight percent and is typically about 0.2 to 1 weight percent. The total of cobalt and manganese in the solid portion of the oxidation reaction mixture can be as high as 4 weight percent. Although the desired 2,6-naphthalene dicarboxylic acid is generally insoluble in the oxidation reaction mixture, particularly when the oxidation reaction mixture is cooled to a temperature below the oxidation reaction temperature, and can be easily separated from the oxidation reaction mixture, the 2,6-naphthalene dicarboxylic acid recovered is also contaminated with trimellitic acid, 2-formyl-6-naphthoic acid, bromo-2-6-naphthalene dicarboxylic acids, other organic impurities and by-products, as well as the cobalt and manganese oxidation metal catalysts. Furthermore, even when the 2,6-naphthalene dicarboxylic acid is separated from the oxidation reaction mixture at an elevated temperature, and even if the separated 2,6-naphthalene dicarboxylic acid is washed with fresh solvent at an elevated temperature to remove residual mother liquor, the recovered 2,6-naphthalene dicarboxylic acid still contains substantial amounts of the aforementioned impurities and by-products which require removal from the 2,6-naphthalene dicarboxylic acid.

Purification process embodying the present invention are conducted in a fixed particulate bed of purification catalyst comprising a noble metal of Group VIII of the Periodic Table of Elements on a titanium dioxide support which does not disintegrate in less than one month under conditions employed in the purification, and in the presence of at most an amount of hydrogen formed by chemical conversions within the catalyst bed at an elevated temperature and at a pressure of at least 5.5 kg/cm$^2$ above the pressure sufficient to maintain the solution substantially in the liquid phase. Both down-flow and up-flow reactors can be used. Crude phthalic acid to be purified is dissolved in water or a like polar solvent. Water is the preferred solvent; however, other suitable polar solvents are the relatively lower molecular weight alkyl carboxylic acids, alone or admixed with water. Aqueous solution contains, typically, from about 5 to about 50 weight percent of the impure dicarboxylic aromatic acid, at a temperature of from about 100° C. to about 350° C. Pressure are in a range upward from at least about 5.5 kg/cm$^2$ above pressure sufficient to maintain the solution substantially in the liquid phase, preferably at least about 7 kg/cm$^2$ above the pressure sufficient to maintain the solution in the liquid phase. Preferably, temperatures are in the range of from about 275° C. to about 300° C.

Decarbonylation reactor pressure conditions primarily depend upon the temperature at which the purification process is carried out. Inasmuch as the temperatures at which practical amounts of the impure phthalic acid may be dissolved are substantially above the normal boiling point of the polar solvent, the process pressures are necessarily considerably above atmospheric pressure to maintain the aqueous solution in liquid phase. If the reactor is hydraulically full, the reactor pressure can be controlled by the feed pumping rate. If the reactor has a head space, the reactor pressure can be maintained by an inert gas such as water vapor and/or nitrogen in the head space. In general, the reactor pressure during decarbonylation can be in the range of about 15 kg/cm$^2$ to about 110 kg/cm$^2$ gauge, and usually is in the range of about 60 kg/cm$^2$ to about 90 kg/cm$^2$ gauge.

The space velocity reported as weight of the crude acid solution per weight of catalyst per hour in the purification step is from about 1 hour$^{-1}$ to about 25 hours$^{-1}$, preferably from about 2 hours$^{-1}$ to about 15 hours$^{-1}$. The residence time of the solution in the catalyst bed varies, depending upon the space velocity.

The decarbonylation reactor can be operated in several modes. For example, a predetermined liquid level can be maintained in the reactor and aqueous solution can be fed in, for any given reactor pressure, at a rate sufficient to maintain the predetermined liquid level. The difference between the actual reactor pressure and the vapor pressure of the aqueous solution present is the partial pressure of inert gas in the reactor vapor space. In yet another operating mode, the decarbonylation reactor can be filled with the aqueous solution so as to provide no reactor vapor space.

In purifying aqueous solutions of crude terephthalic acid that contain 4-carboxybenzaldehyde (4-CBA) according to the present invention, the following principal reactions leading to the formation benzoic acid (BA) and carbon dioxide ($CO_2$) are believed to occur within the initial bed of catalyst comprising a noble metal on a titanium dioxide support, and in the presence of at most an amount of hydrogen formed by chemical conversions

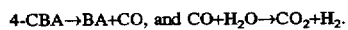

4-CBA→BA+CO, and CO+$H_2O$→$CO_2$+$H_2$.

Decarbonylation and carbon monoxide conversion to carbon dioxide are believed to occur substantially simultaneously in the initial catalyst bed of the present invention. A substantial portion of 4-carboxybenzaldehyde present in the crude terephthalic acid is decarbonylated to benzoic acid and carbon monoxide, most of which CO reacts with water present and is converted to carbon dioxide and hydrogen in the same reactor. Some decomposition of terephthalic acid to benzoic acid also takes place; this is a minor reaction. Thus, effluent aqueous solution from the initial bed contains reduced level of 4-carboxybenzaldehyde and is, advantageously, substantially free of carbon monoxide.

Whereas heretofore the presence of carbon monoxide in effluent from decarbonylation of 4-carboxybenzaldehyde was deemed to be a problem because carbon monoxide is known to inhibit the activity of hydrogenation catalysts, the present process avoids this problem by effecting in the reactor a conversion of at least a substantial portion of the generated carbon monoxide to carbon dioxide by the water-gas shift reaction. Typically, a major portion, if not all, of the generated carbon monoxide is converted to carbon dioxide, which is inert with respect to the purified terephthalic acid and can be readily separated from the resulting reaction product admixture by purging or in any other convenient manner.

Decarbonylation and carbon monoxide conversion to carbon dioxide are believed to occur substantially simultaneously in the first fixed catalyst bed of this invention. The catalyst for the decarbonylation and the carbon monoxide conversion is a carrier-supported metal of Group VIII of the Periodic Table of Elements. The pertinent Periodic Table of Elements can be found on the inside of the back cover of *Handbook of Chemistry and Physics* 53th edition, Chemical Rubber Company, Cleveland, Ohio (1972). Palladium is the preferred catalyst metal; however, rhodium ruthenium and platinum are also suitable. Such catalysts are commercially available.

Catalysts of this invention that are suitable for use in the purification method of this invention are insoluble under the conditions employed therein and comprise at least one supported Group VIII noble metal, whose class includes palladium, rhodium, ruthenium, osmium, iridium, and platinum. The noble metal preferably is at least one of palladium and rhodium and more preferably is palladium. The noble metal component is present on the support at a concentration level in the range of about 0.01 weight percent to about 2 weight percent, based on the total weight of the catalyst, that is, metal plus support, and calculated as the elemental noble metal. Preferably, the catalyst metal loading is about 0.5 weight percent. A typical catalyst of palladium on the support comprises from about 0.01 to about 2 weight percent of palladium, based on the total weight of the catalyst and calculated as elemental metal. The noble metal component can be deposited on the titanium dioxide support by any convenient conventional technique such as spraying or the incipient wetness technique.

The support of the catalyst employed in the purification method of the present invention is titanium dioxide support which does not disintegrate in less than one month under the corrosive conditions that prevail in the purification. Such corrosive conditions are an at least partially, and preferably substantially, aqueous solution of from about 5 to about 50 weight percent of the crude acid being purified and a purification temperature of from about 100° C. to about 350° C. The support is formed by an extrusion technique in any convenient form that can be used in a packed bed.

In one preferred embodiment, at least about one weight percent, preferably at least about 90 weight percent, and more preferably 100 weight percent of the titanium dioxide support is in the rutile crystalline phase.

In another preferred embodiment the titanium dioxide support is formed by calcination of titanium dioxide at a temperature in the range of from about 600° C., preferably from about 800° C., and more preferably from about 900° C., to about 1200° C., preferably to about 1100° C., and more preferably to about 1000° C. In this embodiment, preferably at least 5 weight percent, more preferably at least 70 weight percent and most preferably substantially 100 weight percent, of the titanium dioxide which is calcined is initially in the anatase crystal phase. In addition, the titanium dioxide being calcined contains preferably from about 0.05, more preferably from about 0.2, and most preferably from about 0.5 weight percent, preferably to about 5, and more preferably to about 3 weight percent of a sulfur-containing component, calculated as elemental sulfur.

In yet another preferred embodiment, the calcined titanium dioxide support contains less than 500 parts per million by weight, preferably less than 100 parts per million by weight of a sulfur-containing component, calculated as elemental sulfur.

In a further preferred embodiment, the titanium dioxide support has a total specific surface area of preferably less than about 40 square meters per gram, more preferably less than about 20 square meters per gram, and most preferably less than about 10 square meters per gram.

In another preferred embodiment, the titanium dioxide support has an average pore diameter of at least about 10 nanometers (nm), preferably at least about 20 nm.

In an especially preferred embodiment, at least one weight percent of the titanium dioxide support is in the rutile crystalline phase whose support contains less than 500 parts per million by weight of a sulfur-containing component, calculated as elemental sulfur, has a total specific surface area of less than about 40 square meters per gram, has an average pore diameter of at least about 10 nm, and is formed by calcination at a temperature of from about 600° C. to about 1200° C. of titanium dioxide of which at least 50 weight percent is in the anatase crystal phase and contains at least one weight percent of a sulfur-containing component, calculated as elemental sulfur.

Optionally, effluent aqueous solution from the bed containing noble metal on a titanium dioxide support is passed through a subsequent particulate bed of another purification catalyst in the presence of a molecular hydrogen-containing gas. Hydrogenation of the aqueous solution subsequent to decarbonylation further reduces organic impurities in dicarboxylic aromatic acid recovered by crystallization and separation from the aqueous solution.

The effluent aqueous solution from the bed containing noble metal on a titanium dioxide support is, generally, purified by reduction of impurities therein, for example, by the methods disclosed in the aforesaid U.S. Pat. Nos. 3,584,039; 3,726,915; and 4,405,809. The hydrogenation step according to the present invention for producing purified terephthalic acid, isophthalic acid, or naphthalene dicarboxylic acid is conducted at an elevated temperature and pressure in a fixed catalyst bed. The effluent aqueous solution to be purified contains, typically, from about 5 to about 50 weight percent of the dicarboxylic aromatic acid to be purified dissolved in water or a like polar solvent used in decarbonylation. Although water is the preferred solvent, other suitable polar solvents include the relatively lower molecular weight alkyl carboxylic acids containing from 2 to 6 carbon atoms, typically acetic acid, either alone or admixed with water. When the acid which is being purified is terephthalic acid or isophthalic acid, water is the preferred solvent. When the acid being purified is a naphthalene dicarboxylic acid, a relatively higher purification temperature is employed and a solvent like acetic acid or a mixture of acetic acid and water containing from about 10 to about 90 weight percent of water is the preferred solvent because of its relatively lower vapor pressure. Suitable reactor temperatures for use in this purification step are in the range of from about 100° C. to about 350° C. Preferably, the temperatures employed in the purification step are in the range of about 225° C. to about 300° C.

Pressure employed in the hydrogenation step depends, as in the decarbonylation, primarily upon the temperature employed therein. For example, because temperatures at which practical amounts of impure terephthalic acid may be dissolved in aqueous solvent are substantially above the normal boiling point of the aqueous solvent, process pressures are necessarily considerably above atmospheric pressure to maintain the aqueous solution substantially in a liquid phase. If the reaction is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. In general, the reactor pressure during hydrogenation can be in the range of about 15 kg/cm$^2$ to about 110 kg/cm$^2$ gauge, and usually is in the range of about 60 kg/cm$^2$ to about 90 kg/cm$^2$ gauge.

The reactor employed in the hydrogenation step according to the present invention can be operated in several modes. For example, a predetermined liquid level can be maintained in the reactor and hydrogen be fed in, for any given reactor pressure, at a rate sufficient to maintain the predetermined liquid level. The difference between the actual reactor pressure and the vapor pressure of the crude acid solution present is the hydrogen partial pressure in the reactor vapor space. Alternatively, if hydrogen is fed in admixture with an inert gas such as nitrogen, the difference between the actual reactor pressure and the vapor pressure of the crude acid solution present is the combined partial pressure of hydrogen and the inert gas admixed therewith. In this case the hydrogen partial pressure can be calculated from the known relative amounts of hydrogen and inert gas present in the admixture. In yet another operating mode, the reactor can be filled with the acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen pressure in the reactor preferably is in the range from about 0.5 kg/cm$^2$ to about 20 kg/cm$^2$, and is, typically, in the range of about 0.7 kg/cm$^2$ to about 15 kg/cm$^2$, or higher, depending upon the service pressure rating of the reactor, the degree of contamination of the aforesaid crude acid, the activity and age of the particular catalyst employed, and like processing considerations. In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution. In general, the amount of hydrogen to be supplied to the purification reactor under reaction conditions is, of course, sufficient to effect the desired hydrogenation.

Although the same type of catalyst used in the initial bed for decarbonylation can likewise be used in the subsequent bed for hydrogenation, it is, generally, desirable to select a different preferred catalyst for each bed according to the use therein. In particular, catalysts for use in the hydrogenation step of this invention comprise at least one Group VIII noble metal, whose class includes palladium, rhodium, ruthenium, osmium, iridium, and platinum supported on an active carbon carrier. The noble metal preferably is at least one of palladium and rhodium and more preferably is palladium. The noble metal component is present on the support at a concentration level in the range of about 0.01 weight percent to about 2 weight percent, based on the total weight of the catalyst, that is, metal plus support, and calculated as the elemental noble metal. Preferably, the catalyst metal loading is about 0.5 weight percent. A typical catalyst of palladium on the support comprises from about 0.01 to about 2 weight percent of palladium, based on the total weight of the catalyst and calculated as elemental metal.

Such catalysts are commercially available. A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (Carbon Code CG-5)" and "Rhodium on Activated Carbon Granules (Carbon Code CG-21)." Both of these rhodium-on-carbon catalysts have a $N_2$ BET surface area of about 1,000 $m^2$/gram and have a particle size 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Steam Activated Carbon Granules, Anhydrous."

The catalyst carrier is active carbon, usually that derived from coconut charcoal in the form of granules having a surface area of at least about 600 $m^2$/g ($N_2$; BET Method), preferably about 800 $m^2$/g to about 1,500 $m^2$/g. However, other porous carbonaceous supports or substrates can be used as long as the surface area requirements can be met. In addition to coconut charcoal, activated carbon derived from other plant or from animal sources can be utilized.

The amount of hydrogen supplied under reaction conditions is, of course, sufficient to effect the desired degree of hydrogenation of 4-carboxybenzaldehyde to para-toluic acid. For conversion of 4-carboxybenzaldehyde to para-toluic acid, the stoichiometric hydrogen requirement is two moles of hydrogen for each mole of 4-carboxybenzaldehyde so converted. Preferably, the amount of hydrogen supplied to the catalyst bed is about twice that stoichiometrically required for the foregoing principal reactions that are taking place in the catalyst bed.

Space velocity (pounds of terephthalic acid solution per pound of catalyst per hour) of the aqueous crude terephthalic acid solution through the catalyst bed is about 5 hours$^{-1}$ to about 25 hours$^{-1}$, preferably about 10 hours$^{-1}$ to about 15 hours$^{-1}$. The residence time of the terephthalic acid solution in the catalyst bed varies, depending upon the activity of the catalysts present. In general, however, the residence time of the aqueous terephthalic acid solution in the first catalyst bed is about 100/1 to about 1/100, preferably about 10/1 to about 1/10 and more preferably about 2/1 to about 1/2, of the residence time of the aqueous terephthalic acid solution in the subsequent catalyst bed.

After hydrogenation, the treated acid solution is separated from the solid catalyst particles. The purified acid is crystallized from the separated solution by cooling it, to a temperature for example, about 150° C. or below, that is sufficiently low for crystallization of the purified acid to occur but sufficiently high that the impurities and their reduction products remain dissolved in the resulting mother liquor. Thereafter the mother liquor containing the dissolved impurities and the reduction products is separated from the crystallized purified acid, whereby purified crystals of fiber and thin film grade acid are recovered.

For commercial scale purification of terephthalic acid a continuous mode is preferred. In any event, however, a*-value and b*-value of crude terephthalic acid and purified terephthalic acid are monitored so as to obtain a desired color level of final product, a fiber-grade terephthalic acid.

Terephthalic acid concentration in the solution to be purified by hydrogenation can vary over a relatively wide range. Concentration can be as low as about 5 percent by weight or as high as about 35 percent by weight, based on the weight of the solution. Preferably, the solution concentration of terephthalic acid is in a range of from about 10 to about 30 percent by weight.

The color level of crude terephthalic acid and purified terephthalic acid product can be monitored or evaluated directly or indirectly, as described herein below. Partial pressure of hydrogen in the reactor can be adjusted to compensate for any detected impermissible deviation of the purified terephthalic acid from the desired color level. Adjustment can be made by the procedure taught in U.S. Pat. No. 4,782,181, which is incorporated herein by reference.

In one aspect, color level of crude terephthalic acid and purified terephthalic acid product can be ascertained by measuring its b*-value on the Hunter Color Scale as described in Hunter, The Measurement of Appearance, Chapter 8, pp. 103 to 132, John Wiley & Sons, NY. (1975), and in Wyszecki et al., Color Science Concepts and Methods, Quantitative Data and Formulae, 2d Ed., pp. 166 to 168, John Wiley & Sons, NY.(1982).

More specifically, b*-values of crude terephthalic acid and purified terephthalic acid product can be determined using, for example, a Diano Match Scan Spectrophotometer as follows. A sample of solid product is pressed into a pellet having a thickness of about 0.25 inch and a diameter of about 1 inch. The pellet is then irradiated with white light that has been UV-filtered. The spectrum of visible light reflected from the sample is determined and tristimulus values (X, Y, and Z) are computed using the CIE Standard Observer functions. Using a weighted-ordinate method, tristimulus values are obtained from the following equations:

$$X = \sum_{400}^{700} R\lambda \, x\lambda,$$

$$Y = \sum_{400}^{700} R\lambda \, y\lambda,$$

$$Z = \sum_{400}^{700} R\lambda \, z\lambda,$$

where $R\lambda$ is the percent reflectance of the pellet at wavelength $\lambda$ and $x\lambda$, $y\lambda$, and $z\lambda$, are Standard Observer functions at wavelength 1 for CE Illuminated D65. Tristimulus values x, Y, and Z, identify the color of the pellet in terms of a mixture of primary colors that match it visually. Tristimulus values, however, are of limited use as color specifications, because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts tristimulus values to L*, a*, and b* values as shown below:

$$L^* = 25(100\ Y/Y_0)^{1/3} - 16$$

$$a^* = 500[(X/X_0)^{1/3} - (Y/Y_0)^{1/3}]$$

$$b^* = 500[(Y/Y_0)^{1/3} - (Z/Z_0)^{1/3}]$$

The L* value is a measure of the luminosity or whiteness of an object where a L* value of 100 is pure white, a L* value of 0 is black, and values in a range 0<L*<100 are gray. The L* value is strictly a function of tristimulus Y-value. The b*-value is a measure of a yellowness-blueness attribute where positive b*-values represent yellow appearance and negative b*-values represent blue appearance. The b*-value is a function of both tristimulus values Y and Z.

Alternatively, by the aforesaid indirect method, the color level, e.g., b*-value, of purified terephthalic acid product can be correlated with optical density of (OD) of incoming feed and utilized to adjust the partial pressure of hydrogen in the reactor. Typically, optical density values can be determined using a spectrophotometer and a light beam having wavelength of 340 nanometers (nm) or millimicrons (mμ), correlated with b*-value of purified terephthalic acid product at specific partial pressure of hydrogen for a given catalyst and then used to adjust the partial pressure of hydrogen during a particular process run so as to produce purified product having the desired b*-value.

It has been found that a 0.1 unit deviation in b*-value of purified terephthalic acid product can be compensated by an adjustment in partial pressure of hydrogen in the reactor of as low as about 5 psi to as high as about 60 psi depending upon activity of catalyst employed. If a fresh, relatively high activity catalyst is used, an initial adjustment in partial pressure of hydrogen required for a 0.1 unit deviation in b*-value is, usually, in a range of from about 5 psi to about 7.5 psi. As catalyst stabilizes, however, the adjustment in partial pressure of hydrogen required for a 0.1 unit deviation in b*-value is, usually, in a range of from about 40 psi to about 50 psi.

It has been found that a 0.1 unit change in optical density at 340 nm ($OD_{340}$) of feed solution correlates with about 0.05 unit change in b*-value of purified terephthalic acid product which is obtained from that particular feed solution. Thus, a 0.1 unit change in $OD_{340}$-value of the feed solution can, usually, be compensated by an adjustment in partial pressure of hydrogen in the reactor in a range of from about 2.5 psi to about 4 psi for a fresh, relatively high activity catalyst. As activity of a catalyst stabilizes during use, however, a 0.1 unit change in $OD_{340}$-value of the feed solution can, usually, be compensated by an adjustment in partial pressure of hydrogen in the reactor in a range of from about 20 psi to about 25 psi.

An overall relationship among b*-value, partial pressure of hydrogen in the reactor, and $CD_{340}$ can also be expressed as $$b^*\text{-value} = \alpha A\ (H_{2pp}) + C(OD_{340})$$

where $H_{2pp}$ designates partial pressure of hydrogen in the reactor expressed in psi, $OD_{340}$ is the optical density value of crude terephthalic acid feed solution of the reactor, A is a number in a range of from about 0.001 to about 0.03, and C is a number in a range of from about 0.4 to about 1.4.

Similarly, an overall relationship among b*-value, concentration of hydrogen in the reactor solution, and optical density at 340 nm can be expressed as $$b^*\text{-value} = \alpha D\ (H_{2conc.}) + C(OD_{340})$$

where $H_{2conc.}$ designates concentration of hydrogen in the reactor expressed in cubic centimeters of hydrogen at 1 atmosphere absolute pressure and 0° C. dissolved per gram of crude terephthalic acid feed solution, $OD_{340}$ is the optical density value of crude terephthalic acid feed solution of the reactor, D is a number in a range of from about 0.2 to about 5.75, and C is a number in a range of from about 0.4 to about 1.4.

If it is desired to modulate the concentration of hydrogen in the solution in a hydraulically full reactor directly by adjusting flow of gaseous hydrogen to the hydrogenation reactor, then in such an event hydrogen flow rate can be adjusted to provide a change in concentration of hydrogen in a range of from about 0.03 cc/g to about 0.3 cc/g for a 0.1 unit change in b*-value of the product to be implemented, or in a range of about 0.015 cc/g to about 0.15 cc/g for an observed 0.1 unit change in $OD_{340}$ of feed solution to the hydrogenation reactor.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

In Examples 1 to 3 and Comparative Example A, the relatively impure dicarboxylic acid was crude terephthalic acid prepared in a liquid phase oxidation of para-xylene under conditions of elevated temperature and pressure with oxygen using a cobalt- manganese- and bromine-containing oxidation catalyst in an aqueous solvent containing acetic acid. In Example 4 the terephthalic acid resulting from decarbonylation was further treated by hydrogenation.

Example 1

A pilot plant reactor of the down flow type equipped with a catalyst bed one inch in diameter was used. The end portion of the reactor was fitted with a 20 mesh screen for retaining the catalyst bed in the reactor. The decarbonylation catalyst in the fixed bed is constituted by a palladium-on-rutile titanium dioxide (100 cc, 163 grams) catalyst which contains 0.5 weight percent palladium. The pilot plant reactor was operated at a temperature of about 277° C. (530° F.) at a reactor pressure of about 72 kg/cm² gauge (about 1025 psig). Crude terephthalic acid solution containing about 12 weight percent terephthalic acid and about 2,944 ppm by weight of 4-carboxybenzaldehyde was fed to the reactor at a rate of 1.6 kg of slurry per hour. The effluent from the reactor was cooled to ambient temperature to crystallize the purified terephthalic acid. The purified product was analyzed for 4-carboxybenzaldehyde and other impurities if required. After a line-out period, the average 4-carboxybenzaldehyde conversion was 98.1 percent.

Example 2

The procedure of Example 1 was repeated except that the reactor was charged with 52 grams (32 cc) of palladium-on-rutile titanium dioxide catalyst (0.5 weight percent palladium). After a line-out period of about 110 hours, the average 4-carboxy-benzaldehyde conversion was 62.0 percent. Decarbonylation improved color of the terephthalic acid also. Crude terephthalic acid in the feed had the following color properties: a L* value of 97.3, a* value of −0.65, b* value of 4.31 and an $OD_{340}$ value of 0.68. Whereas the decarbonylated product had the following color properties, on average: a L* value of 97.8, a* value of −0.66, b* value of 2.71 and an $OD_{340}$ value of 0.36.

Example 3

The procedure of Example 1 was repeated except that the reactor was charged with 32 grams (20 cc) of palladium-on-rutile titanium dioxide catalyst (0.5 weight percent palladium). After a line-out period of about 110 hours, the average 4-carboxybenzaldehyde conversion was 53.9 percent.

Comparative Example A

The procedure of Example 1 was repeated except that the reactor was charged with 50 grams (100 cc) of palladium-on-carbon catalyst (0.3 weight percent palladium). After a line-out period of about 110 hours, the average 4-carboxybenzaldehyde conversion was 47.2 percent. Comparative data are shown in Table I.

Example 4

In this example terephthalic acid prepared according to the decarbonylation method of the present invention was further purified by hydrogenation to remove remaining impurities responsible for color and any remaining 4-carboxybenzaldehyde.

A sample of 290 grams of terephthalic acid, prepared by the procedure used in Example 3, in 1160 grams of distilled and deionized water was charged to a one gallon titanium autoclave. Catalyst was 4.85 grams of palladium-on-carbon (0.5 weight percent palladium). After a purge with nitrogen, the reactor was heated to about 277° C. (about 530° F.). Hydrogen and catalyst were added to the reactor for a period of 120 minutes. Analysis of the purified cake indicated the presence of between 1 and 2 ppm weight 2,6-dicarboxyfluorenone (94 percent conversion) and between 15 ppm and 22 ppm by weight 4-carboxybenzaldehyde (99 percent conversion).

The color also improved. Starting feed had the following color properties: L* value of 97.6, a* value of −0.69, b* value of 3.06. Whereas the hydrogenated product had the following color properties: a L* value of 95.0, a* value of 0.04, and b* value of 2.33.

GENERAL

Solids-liquid separations in the following examples are carried out using a 14-inch solid-bowl centrifuge apparatus having a 10-degree beach angle. The centrifuge is operated at speeds up to about 3300 rpm.

The solids-liquid feed used in these examples contains 35 to 45 weight percent solids with a specific gravity of 1.5 in water. Average particle size of the solids varies from about 75 to 150 microns.

Wash liquid is introduced into the separation chamber within the tapered portion of the bowl near a point along the axis of the centrifuge where cake is conveyed out of the liquid pool and onto the drying beach.

Example 5

In this example the procedure of Example 1 was repeated, except that cooling of the aqueous solution to effect crystallization of purified terephthalic acid from mother liquor is by a single step flash depressurization to 100° C., and solids-liquid separation is carried out as described above at 100° C. After a line-out period of about 110 hours, the average 4-carboxy-benzaldehyde conversion was 98 percent.

The resulting aqueous solution, which contains about 59 ppm by weight 4-carboxy-benzaldehyde, about 2612 ppm by weight benzoic acid, and about 423 ppm by weight para-toluic acid, based on terephthalic acid present, is depressurized to ambient pressure and 100° C. Purified terephthalic acid product is, thereafter, recovered from mother liquor while maintaining temperatures during the solids-liquid separation at and below about 100° C. At a wash ratio of 1 pound of wash per pound of feed solids, residual impurities in the discharged cake are reduced to about 30 ppm by weight 4-carboxy-benzaldehyde, about 5 ppm by weight benzoic acid, and about 70 ppm by weight para-toluic acid, based on terephthalic acid present.

Comparative Example B

In this comparative example relatively impure dicarboxylic acid crude terephthalic acid containing 2377 ppm by weight 4-carboxy-benzaldehyde, which is prepared in a liquid phase oxidation of para-xylene under conditions of elevated temperature and pressure with oxygen using a cobalt-manganese- and bromine-containing oxidation catalyst in an aqueous solvent containing acetic acid, is hydrogenated over a Pd on carbon catalyst. Conversion of 4-carboxybenzaldehyde is about 94 percent.

The resulting aqueous solution, which contains about 149 ppm by weight 4-carboxy-benzaldehyde, about 608 ppm by weight benzoic acid, and about 1457 ppm by weight para-toluic acid, based on terephthalic acid present, is depressurized to ambient pressure and 100° C. Purified terephthalic acid product is, thereafter, recovered from mother liquor while maintaining temperatures during the solids-liquid separation at and below about 100° C. At a wash ratio of 1 pound of wash per pound of feed solids, residual impurities in the discharged cake are reduced to about 75 ppm by weight 4-carboxy-benzaldehyde, about 1 ppm by weight benzoic acid, and about 250 ppm by weight para-toluic acid, based on terephthalic acid present.

TABLE I

Decarbonylation of Crude Terephthalic Acid from Liquid Phase Oxidation Using Palladium on Rutile or Carbon[1]

| Catalyst/ Example | 1 | 2 | 3 | A |
|---|---|---|---|---|
| Support | Rutile | Rutile | Rutile | Carbon |
| Palladium, g | 0.815 | 0.26 | 0.16 | 0.15 |
| 4-CBA | | | | |
| Feed, ppm | 2944 | 2944 | 2537 | 2537 |
| Conversion[2], % | 98.1 | 62.0 | 53.9 | 47.2 |
| Color Properties[3] | | | | |
| L* | 96.3 | 97.8 | 96.0 | 97.1 |
| a* | −0.14 | −0.66 | −0.34 | −0.07 |
| b* | 2.15 | 2.71 | 3.93 | 2.14 |
| $OD_{340}$ | 0.26 | 0.36 | 0.39 | 0.19 |

[1]Feed flow rate was about 1.6 kg per hour of 12 weight percent crude terephthalic acid in water.
[2]Average conversion based on difference between concentrations of 4-carboxybenzaldehyde in feed and effluent after about 100 to about 125 hours on stream.
[3]Crude terephthalic acid in feed had the following color properties: L* value of 97.3, a* value of −0.65, b* value of 4.31 and an $OD_{340}$ value of 0.68.

That which is claimed is:

1. A process for purification of a relatively impure terephthalic acid produced by oxidation in the liquid phase of para-xylene with a dioxygen-containing gas at temperatures in a range of from about 120° C. to about 240° C. in the presence of an oxidation catalyst comprising cobalt, manganese, and bromine components, and in a solvent system comprising a $C_1$ to $C_6$ monocarboxylic aliphatic acid, the solvent system containing from 1 weight percent to 20 weight percent of water, which purification comprises:

passing an at least partially aqueous solution of from about 5 to about 50 weight percent of the impure terephthalic acid at a temperature of from about 100° C. to about 350° C. and at a pressure of at least 7 kg/cm² above the pressure sufficient to maintain the solution substantially in the liquid phase, through an initial particulate bed of purification catalyst comprising a noble metal of Group VIII of the Periodic Table of Elements on a titanium dioxide support which does not disintegrate in less than one month under the aforesaid conditions employed in the purification, and in the presence of at most an amount of hydrogen formed by chemical conversions within the initial catalyst bed;

passing effluent aqueous solution from the initial bed through a subsequent particulate bed of purification catalyst comprising at least palladium supported on an active carbon carrier at temperatures of from about 245° C. to about 300° C. and pressures sufficient to maintain the solution substantially in the liquid phase, and in the presence of a molecular hydrogen-containing gas, at space velocities of the aqueous solution through the subsequent bed of particulate catalyst in a range of from about 10 hours⁻¹ to about 15 hours⁻¹;

cooling the aqueous solution to effect separation of purified terephthalic acid from a resulting mother liquor by crystallization; and thereafter recovering purified terephthalic acid product having a total metals content of less than 100 ppm and containing less than 1000 ppm total of 4-carboxybenzaldehyde and para-toluic acid, from the resulting mother liquor while maintaining temperatures within a range downward from about 100° C. to about 25° C.

2. The process according to claim 1 wherein the residence time of aqueous solution in the initial bed of catalyst is from about 10 to about 0.1 of the residence time of the aqueous solution in the subsequent bed of catalyst.

3. The process according to claim 2 wherein the initial bed of catalyst comprises palladium on a titanium dioxide support, and wherein the titanium dioxide support has at least about 90 weight percent of the titanium support in the rutile crystalline phase.

4. A process for purification of a relatively impure terephthalic acid produced by oxidation in the liquid phase of para-xylene with a dioxygen-containing gas at temperatures in a range of from about 120° C. to about 240° C. in the presence of an oxidation catalyst comprising cobalt, manganese, and bromine components, and in a solvent system comprising a $C_1$ to $C_6$ monocarboxylic aliphatic acid, the solvent system containing from 1 weight percent to 20 weight percent of water, which purification comprises:

passing an at least partially aqueous solution of from about 5 to about 50 weight percent of the impure terephthalic acid at a temperature of from about 100° C. to about 350° C. and at a pressure of at least 7 kg/cm² above the pressure sufficient to maintain the solution substantially in the liquid phase, through an initial particulate bed of purification catalyst comprising a noble metal of Group VIII of the Periodic Table of Elements on a titanium dioxide support having at least one weight percent of the titanium dioxide support in the rutile crystalline phase, and in the presence of at most an amount of hydrogen formed by chemical conversions within the initial catalyst bed;

passing effluent aqueous solution from the initial bed through a subsequent particulate bed of purification catalyst comprising at least palladium supported on an active carbon carrier at temperatures of from about 245° C. to about 300° C. and pressures sufficient to maintain the solution substantially in the liquid phase, and in the presence of a molecular hydrogen-containing gas, at space velocities of the aqueous solution through the subsequent bed of particulate catalyst in a range of from about 10 hours⁻¹ to about 15 hours⁻¹, to obtain an effluent aqueous solution from the subsequent bed;

cooling the aqueous solution to effect separation of purified terephthalic acid from a resulting mother liquor by crystallization; and thereafter recovering purified terephthalic acid product, having a maximum para-toluic acid content not exceeding 150 ppm, from the resulting mother liquor while maintaining temperatures within and below the range of from about 100° C. to about 75° C.

5. The process according to claim 4 wherein the residence time of aqueous solution in the initial bed of catalyst is from about 10 to about 0.1 of the residence time of the aqueous solution in the subsequent bed of catalyst.

6. The process according to claim 4 wherein the initial bed of catalyst comprises palladium on a titanium dioxide support, and wherein the titanium dioxide support has at least about 90 weight percent of the titanium support in the rutile crystalline phase.

7. The process according to claim 6 wherein the titanium dioxide support contains less than 500 parts per million by weight of a sulfur-containing component, calculated as elemental sulfur.

8. The process according to claim 6 wherein the subsequent bed of particulate catalyst comprises palladium supported on an active carbon carrier, and the purified dicarboxylic aromatic acid has a total metals content of less than 100 ppm and contains less than 1000 ppm total of 4-carboxybenzaldehyde and para-toluic acid.

9. The process according to claim 6 wherein the resulting purified terephthalic acid has a L*-value in a range of from about 95 to about 100, an a*-value in a range of from about −1 to about +1, and a b*-value in a range of from about 0.5 to about 2.

\* \* \* \* \*

UNITED STATES PATENT AND TRADEMARK OFFICE
CERTIFICATE OF CORRECTION

PATENT NO.: 5,756,833

DATED: May 26, 1998

INVENTOR(S): Bruce I. Rosen, Thomas M. Bartos

It is certified that error appears in the above-identified patent and that said Letters Patent is hereby corrected as shown below:

Patent reads:

| Col. | Line | |
|------|------|---|
| Abstract | | reads "The invention provides...at atmospheric pressure." Entire 2nd paragraph should be deleted |
| 4 | 51 | reads "for Hydrogenation" should read --for hydrogenation-- |
| 12 | 40 | reads "75° C., more preferable while maintaining" should read --75° C., more preferably while maintaining-- |
| 22 | 64 | reads "Tristimulus values x, Y, and Z" should read --Tristimulus values X, Y, and Z-- |
| 23 | 56 | reads "in the reactor, and $CD_{340}$ can also" should read --in the reactor, and $OD_{340}$ can also-- |

Signed and Sealed this

Nineteenth Day of January, 1999

Attest:

Attesting Officer

*Acting Commissioner of Patents and Trademarks*